United States Patent [19]
Kim et al.

[11] Patent Number: 6,063,951
[45] Date of Patent: May 16, 2000

[54] VOLATILE MAGNESIUM ALKYLALUMINUM ALKOXIDE AND DEPOSITION OF MAGNESIUM ALUMINATE FILM USING SAME

[75] Inventors: Yun-Soo Kim; Won-Yong Koh, both of Daejeon; Su-Jin Ku, Taegu, all of Rep. of Korea

[73] Assignee: Korea Research Institute of Technology, Rep. of Korea

[21] Appl. No.: 09/125,225

[22] PCT Filed: Feb. 12, 1997

[86] PCT No.: PCT/KR97/00025

§ 371 Date: Aug. 11, 1998

§ 102(e) Date: Aug. 11, 1998

[87] PCT Pub. No.: WO97/29112

PCT Pub. Date: Aug. 14, 1997

[30] Foreign Application Priority Data

Feb. 12, 1996 [KR] Rep. of Korea .......................... 96-3367

[51] Int. Cl.[7] ................................ C30B 25/00; C07F 5/06
[52] U.S. Cl. .......................... 556/182; 117/104; 117/946; 117/88; 556/181; 556/187; 427/96; 427/99; 427/126.3; 427/126.4; 427/248.1; 427/255
[58] Field of Search ............................. 117/88, 104, 946; 556/187, 27, 181, 182, 190; 427/532, 544, 546, 543, 96, 126.4, 99, 248.1, 255, 126.3, 250, 585; 252/519.2; 106/1.05, 1.25, 287.17

[56] References Cited

U.S. PATENT DOCUMENTS

| | | | |
|---|---|---|---|
| 3,761,500 | 9/1973 | Thomas | 556/182 |
| 3,786,137 | 1/1974 | Thomas | 423/600 |
| 4,543,346 | 9/1985 | Matsui et al. | 501/120 |
| 5,463,001 | 10/1995 | Sano et al. | 526/124.5 |
| 5,805,973 | 9/1998 | Coffinberry et al. | 428/551 |
| 5,922,405 | 7/1999 | Kim et al. | 427/248.1 |
| 5,998,644 | 12/1999 | Kim et al. | 556/28 |

FOREIGN PATENT DOCUMENTS 359027546  2/1984  Japan .

*Primary Examiner*—Benjamin L. Utech
*Assistant Examiner*—Donald L. Champagne
*Attorney, Agent, or Firm*—Anderson Kill & Olick

[57] ABSTRACT

Novel magnesium dialkylaluminum alkoxide derivative represented by $Mg[(\mu-OR')_2AlR_2]_2$ wherein R and R' are each a $C_{1-5}$ alkyl group and R is not the same as R', preferably magnesium dimethylaluminum isopropoxide, is easily prepared by reacting a trialkylaluminum with an alcohol or an aluminum trialkoxide to obtain a dialkylaluminum alkoxide; reacting the dialkylaluminium alkoxide with an alkali metal alkoxide to obtain an alkali metal dialkylaluminum alkoxide; and reacting the alkali metal dialkylaluminum alkoxide with a magnesium halide. The alkoxide derivative of the present invention can be vaporized at a low temperature, below 70° C. and, therefore, effectively employed in the CVD process of a magnesium aluminate film.

8 Claims, No Drawings

6,063,951

VOLATILE MAGNESIUM ALKYLALUMINUM ALKOXIDE AND DEPOSITION OF MAGNESIUM ALUMINATE FILM USING SAME

FIELD OF THE INVENTION

The present invention relates to a novel magnesium alkylaluminum alkoxide derivative having magnesium, aluminum and oxygen in an atomic ratio of 1:2:4; and a process for the preparation thereof. The present invention also relates to a chemical vapor deposition process for coating a substrate with a magnesium aluminate film using said derivative.

BACKGROUND OF THE INVENTION

Magnesium aluminate ($MgAl_2O_4$) is a transparent, chemically stable material having a low permittivity and good resistance to electric and thermal shocks. Magnesium aluminate may be coated on a silicon substrate to form a single crystal film thereof as a buffer layer before coating the substrate with an epitaxial perovskite-type oxide film made of strong dielectrics such as $PbTiO_3$, $BaTiO_3$ and $SrTiO_3$, or of a high temperature superconductor based on copper oxides. The magnesium aluminate buffer layer located between the substrate and the superconductor or dielectric layer may ameliorate many of the problems which occur when the substrate is directly coated with the superconductor or dielectric layer. For example, the magnesium aluminate layer may reduce stress caused by differences in the thermal expansion coefficient and crystal lattices between the coating layer and the substrate. Also, it may prevent the coating material from reacting with the substrate.

There have been reported a number of methods for the preparation of a magnesium aluminate film by using a magnesium aluminum alkoxide represented by $MgAl_2(OR)_8$ wherein the aluminum to magnesium atomic ratio is two as in magnesium aluminate (see U.S. Pat. Nos. 3,761,500 and 3,786,137). Further, the use of an isopropoxide derivative thereof, which is volatile at a low pressure, in chemical vapor deposition (CVD) of a magnesium aluminate has been recently reported (see Jiming Zhang et al., *Journal of Materials Research*, 9, 1333 (1994); and Richard E. Rocheleau et al., *Chemistry of Materials*, 6, 1615 (1994)).

However, it has been reported that in the preparation of the isopropoxide derivative mentioned above, higher molecular weight by-products, e.g., $\{Mg[Al(OPr^i)_4]_2\}_n$ and $Mg_2Al_3(OPr^i)_{13}$ are also produced (see Julian A. Meese-Marktscheffel et al., *Chemistry of Materials*, 5, 755 (1993)). The formation of such high molecular weight by-products leads to lowering of the vapor pressure of $MgAl_2(OPr^i)_8$ in a CVD process to deposit a magnesium aluminate film. Moreover, the above-mentioned magnesium aluminum alkoxide derivative has the disadvantage that it must be heated to about 200° C. or higher when it is used in a CVD process.

A magnesium alkylaluminum alkoxide having the general formula of $Mg[(OR)_2AlR_2]_2$ was first synthesized in the form of a dioxane complex by J. L. Atwood et al. in 1968 (see *Journal of Organometallic Chemistry*, 13, 53(1968)). Recently, Chang et al. reported that $[Me_2Al(\mu—NPr^i{}_2)_2MgMe]_4$ and $[Me_2Al(\mu—NEt_2)_2MgMe]_4$ may be reacted with t-butanol to produce a mixture of $Mg[(\mu—OBu^t)_2AlMe_2]_2$ and $[Me_2Al(\mu—OBu^t)_2Mg(\mu—OBu^t)_2]_2$ (see Cheng-Cheng Chang et al., *Journal of Chemical Society, Dalton Transactions*, 315 (1994)). However, the above method has problems in that the yield is low, the purity of the intended product is low and the starting materials are not easily available.

SUMMARY OF THE INVENTION

It is, therefore, an object of the present invention to provide a novel, volatile magnesium dialkylaluminum alkoxide having the formula of $Mg[(\mu—OR')_2AlR_2]_2$ wherein R and R' are each a $C_{1-5}$ alkyl group and R is not the same as R'.

It is another object of the present invention to present an improved process for the preparation of said alkoxide derivative.

It is a further object of the present invention to teach a process for the preparation of a magnesium aluminate film coated on a substrate.

In accordance with one aspect of the present invention, therefore, there is provided a magnesium dimethylaluminum isopropoxide having the formula of $Mg[(\mu—OPr^i)_2AlMe_2]_2$.

In accordance with another aspect of the present invention, there is presented a process for preparing a magnesium dialkylaluminum alkoxide derivative represented by $Mg[(\mu—OR')_2AlR_2]_2$ wherein R and R' are each a $C_{1-5}$ alkyl group and R is not the same as R', which comprises (i) reacting a trialkylaluminum with an alcohol or an aluminum trialkoxide to obtain a dialkylaluminum alkoxide; (ii) reacting the dialkylaluminum alkoxide with an alkali metal alkoxide to obtain an alkali metal dialkylaluminum alkoxide having the formula of $M[(\mu—OR')_2AlR_2]_2$ wherein R and R' have the same meanings as defined above and M represents Li, Na or K; and (iii) reacting the alkali metal dialkylaluminum alkoxide with a magnesium halide to obtain the desired product.

In accordance with a further aspect of the present invention, there is disclosed a process for coating a substrate with a magnesium aluminate film which comprises contacting the magnesium dialkylaluminum alkoxide derivative, in vapor phase, prepared by the inventive method with the substrate heated to a temperature above 250° C.

DETAILED DESCRIPTION OF THE INVENTION

The novel magnesium dialkylaluminum alkoxide derivative of the present invention has an Mg:Al:O atomic ratio of 1:2:4 as in magnesium aluminate, and has a high vapor pressure. It may be, therefore, advantageously used in a CVD process for depositing a magnesium aluminate film on a substrate. The inventive alkoxide derivative is a complex formed between $Mg(OR')_2$ and $2R_2Al(OR')$, which may be conveniently expressed by a formula, $Mg[(\mu—OR')_2AlR_2]_2$ wherein R and R' are each a $C_{1-5}$ alkyl group and R is not the same as R'. The most preferred in practicing the present invention is magnesium dimethylaluminum isopropoxide represented by $Mg[(\mu—OPr^i)_2AlMe_2]_2$ having the highest vapor pressure among $Mg[(\mu—OR')_2AlR_2]_2$.

In accordance with the present invention, the magnesium dialkylaluminum alkoxide may be produced as follows: (i) a trialkylaluminum is reacted with an alcohol or an aluminum trialkoxide to obtain a dialkylaluminum alkoxide; (ii) the dialkylaluminum alkoxide is reacted with an alkali metal alkoxide to obtain an alkali metal dialkylaluminum alkoxide; and (iii) the alkali metal dialkylaluminum alkoxide is reacted with a magnesium halide to obtain the desired product. The above reaction steps may be shown as follows:

(i) $R_3Al + R'OH \rightarrow R_2AlOR' + RH$ or $2 R_3Al + Al(OR')_3 \rightarrow 3 R_2AlOR'$ (ii) $R_2AlOR' + MOR' \rightarrow M[(\mu - OR')_2AlR_2]_2$ (iii) $2 M[(\mu - OR')_2AlR_2]_2 + MgX_2 \rightarrow Mg[(\mu - OR')_2AlR_2]_2 + MX$ wherein:

R and R' are each a $C_{1-5}$ alkyl group and R is not the same as R';

M represents Li, Na or K; and

X represents Cl, Br or I.

In Step(i), the trialkylaluminum may be reacted with the alcohol in an equivalent ratio at a low temperature ranging from 0 to −78° C., or reacted with the aluminum trialkoxide in a molar ratio of 2:1 at an ambient temperature. Further, in Step (ii), the dialkylaluminium alkoxide and the alkali metal alkoxide may be employed in an equivalent ratio at an ambient temperature, and in Step (iii), the alkali metal dialkylaluminum alkoxide and the magnesium halide may be employed in a molar ratio of 2:1 at an ambient temperature.

The reactions in Steps (i), (ii) and (iii) may be conducted in an organic solvent such as ethers, tetrahydrofuran (THF), benzene, toluene, acetonitrile and hexane and a mixture thereof, preferably under an inert gas atmosphere. The solvent may be preferably dried prior to use.

Alternatively, the dialkylaluminum alkoxide obtained in Step (i) may be directly reacted with a magnesium alkoxide to obtain the desired product, as shown below:

$2 R_2AlOR' + Mg(OR')_2 \rightarrow Mg[(\mu\text{—}OR')_2AlR_2]_2$

Wherein R and R' have the same meanings as defined above.

In addition, all the raw materials described in Steps (i), (ii) and (iii) may be reacted simultaneously to obtain the desired product as follows:

$4 R_3Al + 2 Al(OR')_3 + 6 MOR' + 3 MgX_2 \rightarrow 3 Mg[(\mu\text{—}OR')_2AlR_2]_2 + 6 MX$ wherein R, R', M and X have the same meanings as defined above.

The magnesium dialkylaluminum alkoxides prepared in accordance with the present invention may be preferably vaporized at 70° C. or below, preferably at an ambient temperature.

A magnesium aluminate film may be deposited on a substrate by contacting a vapor of the magnesium dialkylaluminum alkoxide thus obtained with the surface of a substrate preheated at a temperature above 250° C., preferably at a temperature ranging from 300 to 600° C.

The substrate which may be used in practicing the present invention is any inorganic solid that is stable at or above the film deposition temperature and examples thereof include glass, quartz, silicon, gallium arsenide, sapphire, alkali metal niobate, alkaline earth metal titanate, gallium nitride, niobium nitride and the like, among which single crystals of silicon and gallium arsenide are preferred when the coated substrate is intended for use in electronic applications.

The following Examples are provided for the purposes of illustrating certain aspects of the present invention only; they are not to be construed as limiting the scope of the present invention in any way.

In each of Examples, the coated substrate obtained after treatment with the inventive magnesium dialkylaluminum alkoxide was immediately transferred to an X-ray photoelectron spectroscope in order to minimize the exposure thereof to air.

Preparation of Magnesium Alkylaluminum Alkoxides

EXAMPLE 1

Synthesis of magnesium dimethylaluminum isopropoxide, $Mg[(\mu\text{—}OPr^i)_2AlMe_2]_2$ 0.81 g (11.2 mmol) of trimethylaluminum and 1.14 g (5.6 mmol) of aluminum triisopropoxide were dissolved in ethyl ether, and 1.38 g (16.8 mmol) of sodium isopropoxide and 0.80 g (8.4 mmol) of magnesium chloride were added thereto. The resulting mixture was stirred for a day and filtered.

The filtrate thus obtained was distilled under a reduced pressure to remove the solvent and the solid residue was sublimed under a vacuum at 60° C. to obtain 1.22 g (3.26 mmol; yield of 39%) of the title compound in the form of a white solid.

$^1$H NMR analysis in benzene-$d_6$ of the compound thus obtained showed peaks at δ −0.45(singlet, $Al(CH_3)_2$, 12H), 1.08 (doublet, $OCH(CH_3)_2$, 24H) and 3.94(heptet, $OCH(CH_3)_2$, 4H).

EXAMPLE 2

Synthesis of magnesium dimethylaluminum isopropoxide, $Mg[(\mu\text{—}OPr^i)_2AlMe_2]_2$ To a tetrahydrofuran (THF) solution containing 5.09 g (43.8 mmol) of dimethylaluminum isopropoxide, which was previously distilled under a reduced pressure from the reaction mixture of two equivalents of trimethylaluminum and one equivalent of aluminum triisopropoxide, was slowly added 3.60 g (43.8 mmol) of sodium isopropoxide, and the resulting solution was stirred for a day. Thereto was added 2.09 g (21.9 mmol) of magnesium chloride, and the resulting mixture was stirred for a day and filtered.

The filtrate thus obtained was subjected to a reduced pressure treatment to remove the solvent and the solid residue was sublimed under a vacuum at 60° C. to obtain 5.71 g (15.2 mmol; yield of 70 %) of the title compound in the form of a white solid.

EXAMPLE 3

Synthesis of magnesium dimethylaluminum t-butoxide, $Mg[(\mu\text{—}OBu^t)_2AlMe_2]_2$ To a THF solution containing 1.79 g (24.8 mmol) of trimethylaluminum was added 1.73 g (23.3 mmol) of t-butanol dissolved in THF at −70° C., and the mixture was allowed to warm up to ambient temperature while stirring. 2.62 g (23.3 mmol) of potassium t-butoxide was added thereto, and the resulting mixture was stirred for a day. Thereto was added a $MgBr_2$ solution prepared by reacting 0.284 g (11.7 mmol) of magnesium with 2.19 g (11.7 mmol) of 1,2-dibromoethane in THF. The resulting solution was stirred for a day and filtered.

The filtrate thus obtained was distilled under a reduced pressure to remove the solvent and the solid residue was sublimed under a vacuum at 60° C. to obtain 3.48 g (8.08 mmol; yield of 69%) of the title compound in the form of a white powder.

$^1$H NMR analysis in benzene-$d_6$ of the compound thus obtained showed peaks at δ −0.40(singlet, $Al(CH_3)_2$, 12H) and 1.27(singlet, $OC(CH_3)_3$, 36H).

EXAMPLE 4

Synthesis of magnesium diethylaluminum isopropoxide, $Mg[(\mu—OPr^i)_2AlEt_2]_2$ 3.13 g (27.4 mmol) of triethylaluminum (Aldrich, 93%) and 2.80 g (13.7 mmol) of aluminum triisopropoxide were dissolved in ethyl ether and stirred for a day. 3.38 g (41.2 mmol) of sodium isopropoxide was added thereto, and the resulting mixture was stirred for a day. Thereto was added 1.96 g (20.6 mmol) of magnesium chloride, the resulting solution was stirred for a day and filtered.

The filtrate thus obtained was subjected to a reduced pressure treatment to remove the solvent, and 6.28 g (14.6 mmol; yield of 71%) of the title compound was obtained in the form of a liquid.

$^1$H NMR analysis in benzene-$d_6$ of the compound thus obtained showed peaks at δ 0.15(quartet, $Al(CH_2CH_3)_2$, 8H), 1.11 (doublet, $OCH(CH_3)_2$, 24H), 1.35(triplet, $Al(CH_2CH_3)_2$, 12H) and 3.95(heptet, $OCH(CH_3)_2$, 4H).

Deposition of Magnesium Aluminate Film

EXAMPLE 5

The compound prepared in Example 1 was vaporized at room temperature and the vapor thereof was conveyed to a Si(100) substrate preheated to 600° C. for 4 hours to deposit a film thereon. The X-ray photoelectron spectrum of the deposited film showed peaks corresponding to magnesium, aluminum, oxygen and carbon, but not the peaks for silicon. The elemental composition of the film surface determined by comparing the photoelectron peak areas corresponded to an Mg:Al:O atomic ratio of 1.0:2.4:6.6. The XRD diffraction pattern of the deposited film showed broad peaks at 2Θ=31.3, 36.9 and 44.8°, which coincide with characteristic peaks diffracted from (220), (311) and (400) planes of magnesium aluminate.

EXAMPLE 6

The compound prepared in Example 3 was vaporized at 60° C. and the vapor thereof was conveyed to a Si(100) substrate preheated to 400° C. for 1.5 hours to deposit a film thereon. The X-ray photoelectron spectrum of the deposited film showed peaks corresponding to magnesium, aluminum, oxygen and carbon, but not the peaks for silicon. The elemental composition of the film surface determined by comparing the photoelectron peak areas corresponded to an Mg:Al:O atomic ratio of 1.0:2.3:5.6.

EXAMPLE 7

The compound prepared in Example 3 was vaporized at 60° C. and the vapor thereof was conveyed to a GaAs(100) substrate preheated to 400° C. for 1 hour and 15 minutes to deposit a film thereon. The X-ray photoelectron spectrum of the deposited film showed peaks corresponding to magnesium, aluminum, oxygen and carbon, but not the peaks for Ga or As. The elemental composition of the film surface determined by comparing the photoelectron peak areas corresponded to an Mg:Al:O atomic ratio of 1.0:2.2:6.0.

EXAMPLE 8

The compound prepared in Example 4 was vaporized at 70° C. and the vapor thereof was conveyed to a Si(100) substrate preheated to 400° C. for 6 hours to deposit a film thereon. The X-ray photoelectron spectrum of the deposited film showed peaks corresponding to magnesium, aluminum, oxygen and carbon, but not the peaks for silicon. The elemental composition of the film surface determined by comparing the photoelectron peak areas corresponded to an Mg:Al:O atomic ratio of 1.0:1.8:5.2.

As shown above, the magnesium dialkylaluminum alkoxide derivative of the present invention can be vaporized at a low temperature, below 70° C., and therefore, it may be effectively employed in the CVD of a magnesium aluminate film. In addition, the alkoxide derivative of the present invention may be used in the production of a magnesium aluminate powder and in the chemical vapor infiltration (CVI) of porous materials.

While the invention has been described with respect to the specific embodiments, it should be recognized that various modifications and changes may be made by those skilled in the art to the invention which also fall within the scope of the invention as defined by the appended claims.

We claim:

1. Magnesium dimethylaluminum isopropoxide having the formula of $Mg[(\mu—OPr^i)_2AlMe_2]_2$.

2. A process for preparing a magnesium dialkylaluminum alkoxide represented by $Mg[(\mu—OR')_2AlR_2]_2$ wherein R and R' are each a $C_{1-5}$ alkyl group and R is not the same as R', which comprises (i) reacting a trialkylaluminum with an alcohol or an aluminum trialkoxide to obtain a dialkylaluminum alkoxide; (ii) reacting the dialkylaluminium alkoxide with an alkali metal alkoxide to obtain an alkali metal dialkylaluminum alkoxide represented by $M[(\mu—OR')_2AlR_2]_2$ wherein R and R' have the same meanings as defined above and M represents Li, Na or K; and (iii) reacting the alkali metal dialkylaluminum alkoxide with a magnesium halide to obtain the magnesium dialkylaluminum alkoxide.

3. The process of claim 2 wherein the magnesium dialkylaluminum alkoxide is magnesium dimethylaluminum isopropoxide represented by $Mg[(\mu—OPr^i)_2AlMe_2]_2$.

4. A process for coating a substrate with a magnesium aluminate film which comprises contacting a vapor of a magnesium dialkylaluminum alkoxide represented by $Mg[(\mu—OR')_2AlR_2]_2$ wherein R and R' are each a $C_{1-5}$ alkyl group and R is not the same as R', with the substrate heated to a temperature above 250° C.

5. The process of claim 4 wherein the magnesium dialkylaluminum alkoxide is magnesium dimethylaluminum isopropoxide represented by $Mg[(\mu—OPr^i)_2AlMe_2]_2$.

6. The process of claim 5 wherein the magnesium dimethylaluminum isopropoxide is vaporized at a temperature ranging from 0 to 70° C.

7. The process of claim 4 wherein the substrate is a single crystal of silicon or gallium arsenide.

8. The process of claim 4 wherein the substrate is of a semiconductor material.

* * * * *